(12) United States Patent
Saka et al.

(10) Patent No.: US 8,409,832 B2
(45) Date of Patent: Apr. 2, 2013

(54) METHOD FOR PRODUCING ACETIC ACID USING ANAEROBIC MICROORGANISM AND METHOD FOR PRODUCING BIOETHANOL

(75) Inventors: Shiro Saka, Otsu (JP); Hisashi Miyafuji, Kyoto (JP); Yoshihito Kohara, Suita (JP); Haruo Kawamoto, Kyoto (JP)

(73) Assignee: Shiro Saka, Otsu shi, Shiga (JP)

( * ) Notice: Subject to any disclaimer, the term of this patent is extended or adjusted under 35 U.S.C. 154(b) by 277 days.

(21) Appl. No.: 13/039,563

(22) Filed: Mar. 3, 2011

(65) Prior Publication Data

US 2012/0053368 A1 Mar. 1, 2012

(30) Foreign Application Priority Data

Aug. 31, 2010 (JP) ................. 2010-193142

(51) Int. Cl.
*C12P 7/54* (2006.01)
*C12P 7/06* (2006.01)

(52) U.S. Cl. ......... 435/140; 435/161; 560/129; 560/231

(58) Field of Classification Search ................... 435/140, 435/161; 560/129, 231
See application file for complete search history.

(56) References Cited

U.S. PATENT DOCUMENTS

2008/0193989 A1 8/2008 Verser

FOREIGN PATENT DOCUMENTS

| JP | 2002537848 | 11/2002 |
| JP | 2009106274 | 5/2009 |
| JP | 2010517581 | 5/2010 |
| WO | 0053791 A1 | 9/2000 |

OTHER PUBLICATIONS

Yoshihito Kohara, Hisashi Miyafuji, Shiro Saka : Abstracts of The 60th Annual Meeting of The Japan Wood Research Society, p. 165 Mar. 17-19, 2010.

*Primary Examiner* — Elvis O Price
(74) *Attorney, Agent, or Firm* — Roberts Mlotkowski Safran & Cole P.C.

(57) ABSTRACT

To provide a method for producing acetic acid from lignocellulose with high efficiency and a method for producing bioethanol.
First, lignocellulose such as wood is decomposition-treated by a method such as pressurized hydrothermal treatment (Step S1). Then, the treatment solution obtained in Step S1 is acetic acid-fermented as a substrate using *Clostridium thermoaceticum* as an anaerobic microorganism in the presence of cysteine hydrochloride monohydrate at a concentration of 0.05 to 0.1 g/L (Step S2).

9 Claims, 8 Drawing Sheets

METHOD FOR PRODUCING ACETIC ACID USING ANAEROBIC MICROORGANISM AND METHOD FOR PRODUCING BIOETHANOL

TECHNICAL FIELD

The present invention relates to methods for producing acetic acid using an anaerobic microorganism and methods for producing bioethanol using the production methods. More specifically, it relates to methods for producing acetic acid by acetic acid fermentation of a substrate including a treatment solution obtained by decomposition treatment such as pressurized hydrothermal treatment of lignocellulose, and methods for producing ethanol by esterification and hydrogenation of the acetic acid.

BACKGROUND ART

Bioethanol means ethanol derived from biological sources and is mainly produced by fermentation of carbohydrates contained in juice and the like from sugarcane and beet or of saccharified products of starch contained in corn, sweet potato, and the like (see Patent Document 1). For example, in the method according to Patent Document 1, saccharides (carbohydrates) are fermented to prepare acetic acid that is esterified and hydrogenated to produce ethanol.

In the production method of ethanol according to Patent Document 1, the fermentation process includes two steps of lactic acid fermentation and acetic acid fermentation. Furthermore, the acetic acid fermentation employs *Clostridium* bacteria, specifically, acetogenic bacteria such as *Clostridium thermoaceticum* and *Clostridium formicoaceticum*.

There has been also developed a method for producing ethanol using biomass resources as a material (see Patent Document 2). In the method according to Patent Document 2, acidic hydrolysis or enzymatic hydrolysis of cellulose that is contained in biomass resources produces fermentative carbohydrates. Furthermore, the inventors of the present invention have developed a method in which lignocellulose is treated with pressurized hot water to prepare a wide variety of saccharides, the saccharides are converted into acetic acid by acetic acid fermentation, and the acetic acid is esterified and hydrogenated to produce ethanol (see Patent Document 3).

CITATION LIST

Patent Document

[Patent Document 1] JPA 2002-537848
[Patent Document 2] JPA 2010-517581
[Patent Document 3] JPA 2009-106274

DISCLOSURE OF THE INVENTION

Technical Problems to be Solved

However, the conventional techniques described above have a problem of a low conversion efficiency to ethanol. For example, in conventional methods for producing bioethanol using saccharides or starch as a material, 1 mol of glucose ($C_6H_{12}O_6$) usually produces 2 mol of ethanol ($C_2H_5OH$) and 2 mol of carbon dioxide ($CO_2$) as shown in Chemical Formula (1), while such methods have low carbon availability because only four carbons are used among six carbons in glucose for producing ethanol.

$$C_6H_{12}O_6 \rightarrow 2C_2H_5OH + 2CO_2 \tag{1}$$

In contrast, methods for producing bioethanol through acetic acid, such as the methods according to Patent Documents 1 to 3, can improve production efficiency of ethanol theoretically. However, for example, the method according to Patent Document 1 has a problem of complicated process, that is, the lactic acid fermentation is required before the acetic acid fermentation for obtaining acetic acid. Furthermore, the method according to Patent Document 2 has a problem of unclear information about, for example, a pretreatment method for a material, a compound obtained by the treatment, and productivity of acetic acid after the pretreatment.

The method according to Patent Document 3 can produce ethanol from a substrate in a treatment solution more efficiently than the conventional methods described above because lignocellulose is decomposed into saccharides by pressurized hydrothermal treatment and a microorganism used can convert all of the various saccharides into acetic acid. However, its conversion ratio from saccharides into acetic acid is insufficient.

In view of the above, the present invention has an object to provide a method for producing acetic acid by which acetic acid can be produced from lignocellulose with high efficiency and a method for producing bioethanol.

Means to Solve the Problems

The inventors of the invention have revealed in previous studies that a mixed fermentation system using two microorganisms, *Clostridium thermoaceticum* and *Clostridium thermocellum*, can convert a substrate including a wide variety of compounds such as hexoses, pentoses, oligosaccharides of them, and glucuronic acid that are obtained by pressurized hydrothermal treatment of wood into acetic acid. In addition, the inventors have carried out intensive studies in order to solve the problems in the method for producing acetic acid using the anaerobic microorganisms, and as a result, have obtained findings described below.

The inventors have firstly studies on the reason of a lower conversion ratio to acetic acid than the theoretical value, and have found that (i) a substrate added is used in large amounts for growth of the microorganisms and thus is insufficient for metabolism to acetic acid and that (ii) a nutrient solution or a buffer solution used in a fermentation medium reduces the substrate. Then, the inventors have found that "reduction of the amount of cysteine added into the nutrient solution suppresses the growth of microorganisms" in order to solve the problem (i) and that "addition of a buffer solution to the fermentation system is not required when fermentation is performed while adding an aqueous alkali solution, as needed, based on pH of the culture medium monitored with a pH meter" in order to solve the problem (ii), and the invention has been completed.

Namely, in an aspect of the invention, a method for producing acetic acid includes a step of acetic acid-fermenting a substrate including a treatment solution obtained by decomposition treatment of lignocellulose using an anaerobic microorganism including *Clostridium thermoaceticum* in the presence of cysteine hydrochloride monohydrate at a concentration of 0.05 to 0.1 g/L.

Here, "decomposition treatment" means hydrothermal treatment such as pressurized hydrothermal treatment, blasting treatment, acidic hydrolysis, alkaline treatment, enzymatic decomposition, and the like.

In the invention, the reduction of the amount of cysteine hydrochloride monohydrate added from 0.05 to 0.1 g/L suppresses the growth of microorganisms during fermentation.

As a result, the amount of the substrate to be converted into acetic acid is increased to improve the conversion efficiency into acetic acid.

In the production method, an aqueous alkali solution may be added on the basis of solution pH measured with a pH meter to maintain a solution pH within 6.5 to 7.5 during fermentation in the acetic acid fermentation step.

During the acetic acid fermentation, *Clostridium thermocellum* may be used as the anaerobic microorganism in combination with *Clostridium thermoaceticum*.

The method may further include a step of pressurized hydrothermal-treating lignocellulose to prepare a treatment solution, and the treatment solution may be used as the substrate in the acetic acid fermentation step.

In this case, it is preferable that the pressurized hydrothermal treatment is performed at a pressure of 0.11 to 50 MPa and a temperature of 130 to 400° C. for 0.1 second to 60 minutes.

The pressurized hydrothermal treatment may include, for example, a first treatment stage at a pressure of 0.11 to 50 MPa and a temperature of 130 to 270° C. for 1 to 60 minutes and a second treatment stage at a pressure of 0.11 to 50 MPa and a temperature of 230 to 400° C. and higher than the temperature in the first stage for 0.1 second to 60 minutes.

The substrate may comprise at least a compound selected from the group consisting of hexoses, pentoses, glucuronic acid, organic acids, excessively decomposed saccharides and lignin-derived compounds.

The lignin-derived compounds may comprise at least a compound selected from the group consisting of guaiacol, syringol, vanillin, syringaldehyde, coniferyl aldehyde, sinapyl aldehyde, coniferyl alcohol and sinapyl alcohol.

In another aspect of the invention, a method for producing bioethanol includes a step of esterifying and hydrogenating the acetic acid produced by the method for producing acetic acid to produce ethanol.

EFFECT OF THE INVENTION

The invention can suppress the growth of microorganisms because cysteine hydrochloride monohydrate is added in a lower amount than that in conventional methods, and therefore acetic acid can be produced from lignocellulose with high efficiency.

BEST MODE FOR CARRYING OUT THE INVENTION

Hereinafter, embodiments for carrying out the invention will be described in detail with reference to the accompanying drawings. However, the invention is not limited to the embodiments described below.

<First Embodiment>

First, a method for producing acetic acid according to a first embodiment of the invention will be described. The method for producing acetic acid of the embodiment includes a step of decomposition-treating lignocellulose (Step S1) and a step of acetic acid-fermenting the treatment solution obtained in Step S1 as a substrate using *Clostridium thermoaceticum* as an anaerobic microorganism in the presence of cysteine hydrochloride monohydrate (hereinafter simply referred to as cysteine) at a concentration of 0.05 to 0.1 g/L (Step S2).

[Step S1: Decomposition Treatment Step]

Lignocellulose is a main chemical component of wood and is composed of cellulose, hemicellulose, lignin, and the like. Decomposition treatment of the lignocellulose generates various monosaccharides, oligosaccharides, polysaccharides, excessively decomposed saccharides, organic acids, lignin-derived compounds, and the like. Examples of the treatment method include, but are not necessarily limited to, hydrothermal treatment such as pressurized hydrothermal treatment, blasting treatment, acidic hydrolysis, alkaline treatment, and enzymatic decomposition.

Among these decomposition treatment methods, the pressurized hydrothermal treatment is particularly preferred. Examples of the condition in the pressurized hydrothermal treatment of lignocellulose include, but are not necessarily limited to, a pressure of 0.11 to 50 MPa, a temperature of 130 to 400° C., and a treatment time of 0.1 second to 60 minutes. Such pressurized hydrothermal treatment can decompose lignocellulose with water alone without a catalyst and the like and can reduce the reaction time.

The pressurized hydrothermal treatment may be performed twice or more times under varied conditions. For example, for two-step treatment, the first treatment stage may be performed at a pressure of 0.11 to 50 MPa and a temperature of 130 to 270° C. for 1 to 60 minutes, and then, the second treatment stage may be performed at a pressure of 0.11 to 50 MPa and a temperature of 230 to 400° C. and higher than the temperature in the first stage for 0.1 second to 60 minutes. Such two-step treatment can treat components having reactivity different to each other, such as hemicellulose and cellulose, under a reaction condition suitable for each component. However, the range of the pressure and temperature of the pressurized hydrothermal treatment are not limited to ranges above. Those ranges may be changed properly, considering such as specifications of the device.

[Step S2: Acetic Acid Fermentation Step]

In the method for producing acetic acid of the embodiment, anaerobic acetic acid fermentation is performed using the treatment solution obtained in Step S1 as a substrate and using an anaerobic *Clostridium* species, *Clostridium thermoaceticum*. The anaerobic acetic acid fermentation is a fermentation method in the absence of oxygen. For example, the fermentation can directly convert saccharides such as glucose into acetic acid as shown in Chemical Formula (2). In the method for producing acetic acid of the embodiment, it is possible to convert not only saccharides but also lignin-derived compounds into acetic acid. On this account, the method has high carbon availability and thus can improve the productivity of acetic acid as compared with aerobic acetic acid fermentation that produces acetic acid by oxidation of ethanol.

$$C_6H_{12}O_6 \rightarrow 3CH_3COOH \quad (2)$$

(Anaerobic Microorganism)

Anaerobic microorganisms used in the anaerobic acetic acid fermentation can be suitably selected depending on components contained in a decomposition treatment solution of lignocellulose as the substrate, but the method for producing acetic acid of the embodiment employs at least *Clostridium thermoaceticum* as an anaerobic *Clostridium* species. Table 1 shows substrates that can be metabolized by the acetic acid fermentation of various anaerobic microorganisms.

TABLE 1

| microorganism | metabolizable substrate | | |
|---|---|---|---|
| | hexose | pentose | polysaccharide |
| *Clostridium thermoaceticum* | O | O | X |
| *Clostridium thermoautorophicum* | O | O | X |
| *Clostridium aceticum* | O | O | X |
| *Clostridium formicaceticum* | O | X | X |
| *Acetobacterium woodii* | O | — | X |
| *Sarcina ventriculi* | O | O | X |
| *Clostridium thermocellum* | X | X | O |
| *Clostridium lentocellum* SG6 | O | O | O |

As shown in Table 1, *Clostridium thermoaceticum* metabolizes monosaccharides as substrates and can convert hexoses (glucose, mannose, galactose, fructose, and rhamnose), pentoses (xylose and arabinose), glucuronic acid as an acidic saccharide, organic acids (formic acid and lactic acid), as well as some excessively decomposed saccharides (5-hydroxymethylfurfural, furfural, erythrose, glycolaldehyde, and methylglyoxal), and lignin-derived compounds (guaiacol, syringol, vanillin, syringaldehyde, coniferyl aldehyde, sinapyl aldehyde, coniferyl alcohol, and sinapyl alcohol) into acetic acid.

Figure 1:
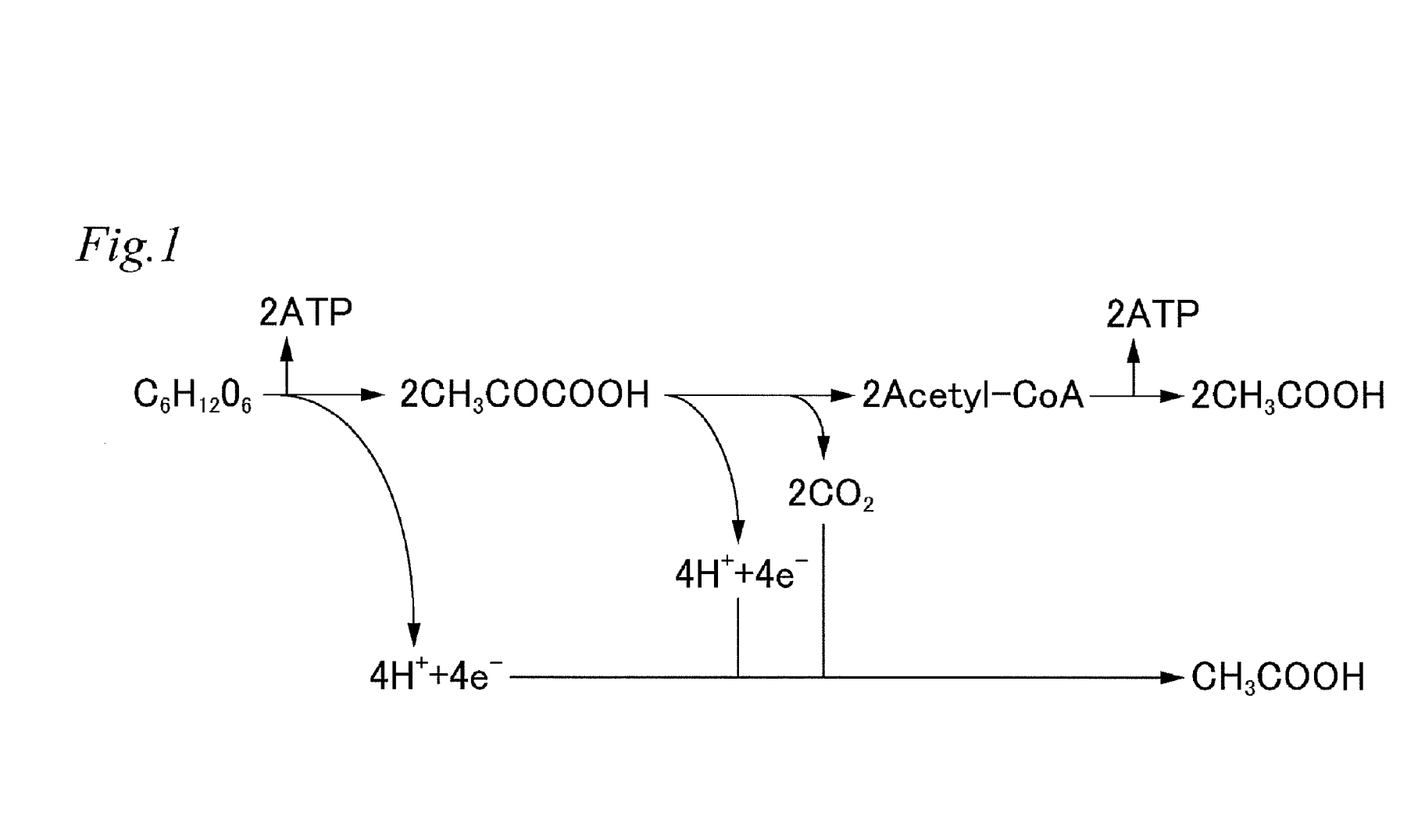
FIG. 1 is a view showing a fermentation pathway from a hexose to acetic acid by *Clostridium thermoaceticum*.

FIG. 1 is a view showing a fermentation pathway from a hexose to acetic acid by *Clostridium thermoaceticum*. In FIG. 1, ATP means adenosine triphosphate and Acetyl-CoA means acetyl coenzyme A. *Clostridium thermoaceticum* can convert a hexose into acetic acid not through ethanol as shown in FIG. 1 and has characteristics that the conversion efficiency is excellent and the amount of products other than acetic acid is small.

However, the *Clostridium thermoaceticum* can convert neither polysaccharides nor oligosaccharides. Therefore, another anaerobic microorganism is preferably used in combination with *Clostridium thermoaceticum* in order to convert a wider variety of substrates into acetic acid. Specifically, *Clostridium thermocellum* is preferably used in combination with *Clostridium thermoaceticum*.

*Clostridium thermocellum* metabolizes polysaccharides as substrates. It decomposes celluloses with high efficiency and can convert, for example, hemicelluloses such as xylan and mannan in addition to celluloses. The *Clostridium thermocellum* cannot convert monosaccharides such as glucose and xylose and has a lower conversion efficiency into acetic acid than that of *Clostridium thermoaceticum*. However, the combination use with *Clostridium thermoaceticum* complements the function and can perform the conversion into acetic acid with high efficiency.

The inventors of the invention have ascertained this by experiments. For example, when cellulose as a polysaccharide was fermented as a substrate using *Clostridium thermocellum* alone, the conversion efficiency into acetic acid was less than 30%, but when *Clostridium thermoaceticum* and *Clostridium thermocellum* were used in combination, acetic acid was produced at a conversion efficiency of 60.5%.

Such combination use further provides an advantage that *Clostridium thermocellum* converts polysaccharides into lower molecular compounds and *Clostridium thermoaceticum* converts the produced monosaccharides into acetic acid. Namely, the combination use of *Clostridium thermoaceticum* and *Clostridium thermocellum* can produce acetic acid with high efficiency from a wide variety of substances obtained by pressurized hydrothermal treatment of woody biomass.

(Amount of Cysteine Added: 0.05 to 0.1 g/L)

The anaerobic acetic acid fermentation is performed as follows: to a substrate (decomposition treatment solution of lignocellulose), a culture medium of the anaerobic microorganism, a buffer solution, and a nutrient solution are added; and the whole is stirred in an oxygen free atmosphere at a predetermined temperature for a predetermined period of time. The nutrient solution used for the fermentation can be properly prepared depending on the type of anaerobic microorganisms, but cysteine is added into the nutrient solution for *Clostridium thermoaceticum*.

Cysteine plays not only a role to supply sulfur that is essential for the growth of *Clostridium thermoaceticum* but also a role as a reducing agent to properly maintain the redox balance in a solution. However, as described above, if cysteine is contained in the nutrient solution in a large amount, a large amount of a substrate is used for the growth of microorganisms to reduce the conversion efficiency into acetic acid.

Hence, in the method for producing acetic acid of the embodiment, the amount of cysteine added into the nutrient solution is set to 0.05 to 0.1 g/L that is lower than in conventional methods. This suppresses the growth of *Clostridium thermoaceticum* and accelerates the metabolism into acetic acid.

A cysteine content of more than 0.1 g/L in the nutrient solution increases the growth of microorganisms to reduce the conversion efficiency into acetic acid. A cysteine content of less than 0.05 g/L in the nutrient solution can suppress the growth of microorganisms but also reduces the conversion efficiency into acetic acid.

(Solution pH Adjustment During Fermentation)

As described above, the inventors of the invention have found that a buffer solution decomposes saccharides in a substrate solution. Specifically, it is supposed that saccharides are chemically reacted with salts by heat to be decomposed. Thus, it is preferable that an aqueous alkali solution such as an aqueous sodium hydroxide solution is added without the buffer solution to adjust the solution pH during fermentation in order to further increase the conversion efficiency into acetic acid.

Examples of the specific method include a method in which an aqueous alkali solution is added, as needed, on the basis of solution pH monitored with a pH meter during fermentation to maintain a solution pH within 6.5 to 7.5 during fermentation. As a result, the solution pH can be maintained in an appropriate range during fermentation without a buffer solution, and therefore the reduction of a substrate can be suppressed to further increase the fermentation efficiency into acetic acid.

As described above in detail, in the method for producing acetic acid of the embodiment, the growth of microorganisms can be suppressed because the amount of cysteine added is reduced than in conventional methods during anaerobic acetic acid fermentation that uses the decomposition treatment solution of lignocellulose as a substrate and that uses *Clostridium thermoaceticum*. As a result, the reduction of the substrate by the growth of microorganisms is suppressed to improve the conversion efficiency from the substrate into acetic acid.

In addition to the reduced amount of cysteine, the addition of an aqueous alkali solution for adjusting pH without a buffer solution during fermentation prevents the decomposition of the substrate by the buffer solution. This operation can improve the conversion efficiency into acetic acid to a higher degree.

<Second Embodiment>

Figure 2:
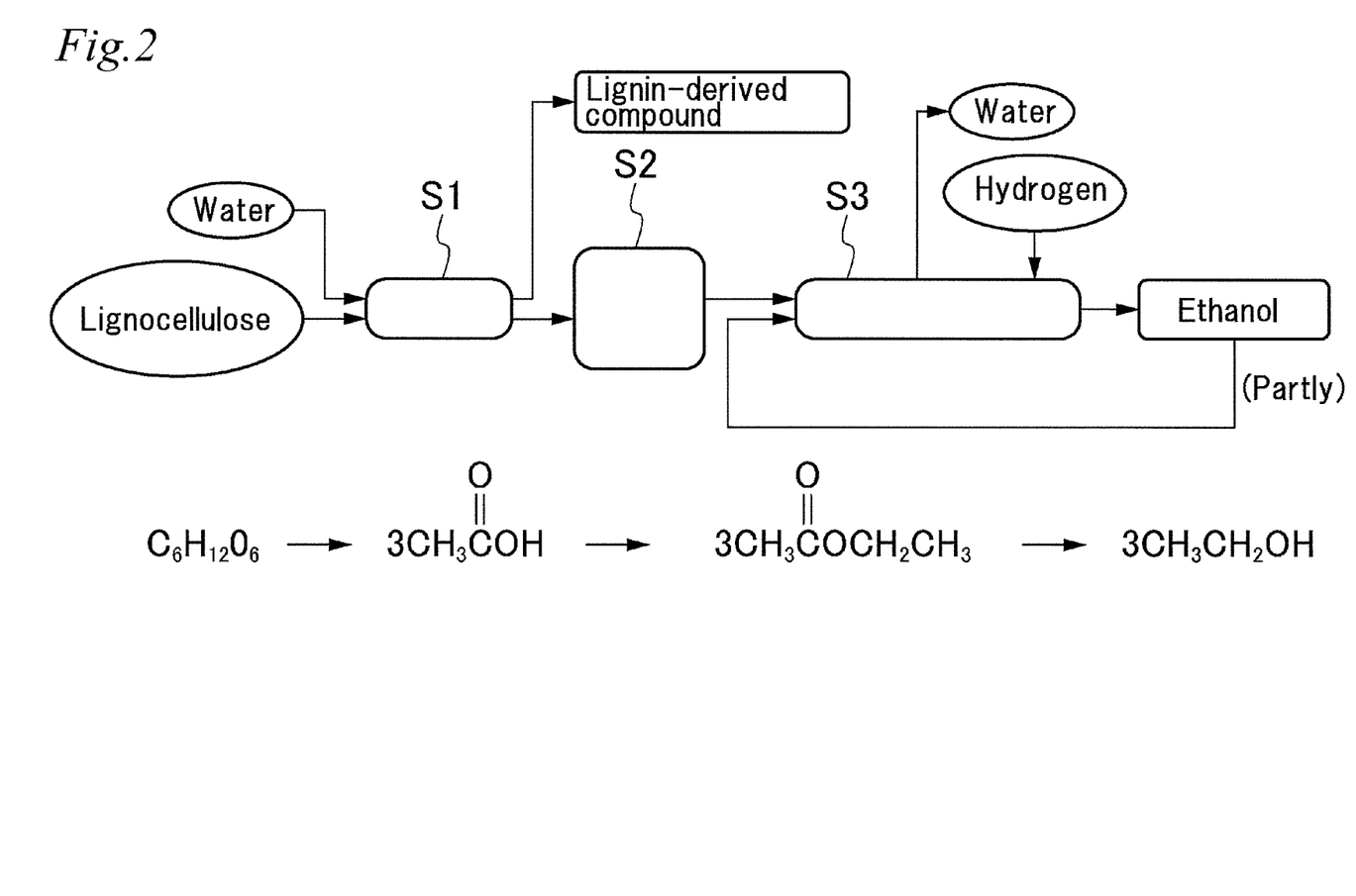
FIG. 2 is a schematic view showing a method for producing bioethanol according to a second embodiment of the invention.

Next, a method for producing bioethanol according to a second embodiment of the invention will be described. FIG. 2 is a schematic view showing a method for producing bioethanol of the embodiment. The method for producing bioethanol of the embodiment is a method that produces bioethanol using the method for producing acetic acid of the first embodiment. In the method, the acetic acid produced by the method for producing acetic acid of the first embodiment is esterified and then hydrogenated to produce ethanol.

Specifically, as shown in FIG. 2, the method for producing bioethanol of the embodiment include a step of decomposition-treating lignocellulose (Step S1), a step of acetic acid-fermenting the treatment solution obtained in Step S1 as a substrate using *Clostridium thermoaceticum* in the presence of cysteine hydrochloride monohydrate at a concentration of 0.05 to 0.1 g/L (Step S2), and a step of producing ethanol from the acetic acid obtained in Step S2 (Step S3).

Hereinafter, each step will be described in detail. However, the decomposition treatment step (Step S1) and the acetic acid fermentation step (Step S2) will not be described because each step is the same as that in the first embodiment.

[Step S3: Ethanol Producing Step]

Figure 3:
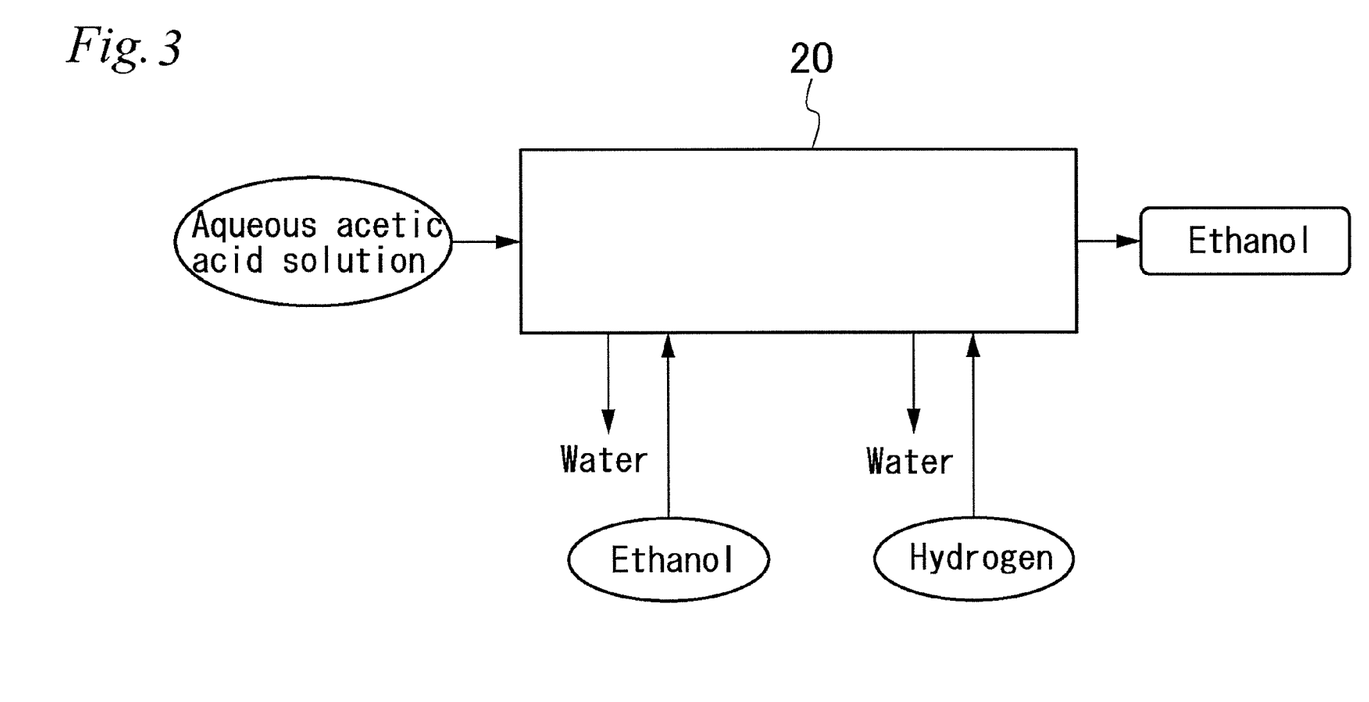
FIG. 3 is a schematic view showing an apparatus for producing ethanol from an aqueous acetic acid solution.

FIG. 3 is a schematic view showing an apparatus for producing ethanol from an aqueous acetic acid solution. In the ethanol producing step of Step S3, esterification shown in Chemical Formula (3) and hydrogenation shown in Chemical Formula (4) are carried out. These reactions can be carried out using, for example, an apparatus 20 for producing ethanol as shown in FIG. 3 in one step.

$$3CH_3COOH + 3C_2H_5OH \rightarrow 3CH_3COOC_2H_5 + 3H_2O \quad (3)$$

$$3CH_3COOC_2H_5 + 6H_2 \rightarrow 6C_2H_5OH \quad (4)$$

In the apparatus 20 for producing ethanol shown in FIG. 3, an introduced aqueous acetic acid solution is firstly dehydrated and concentrated, and then, acetic acid ($CH_3COOH$) is reacted with ethanol ($C_2H_5OH$) to produce ethyl acetate ($CH_3COOC_2H_5$) while removing the formed water ($H_2O$). Next, the obtained ethyl acetate ($CH_3COOC_2H_5$) is reacted with hydrogen ($H_2$) to produce ethanol ($C_2H_5OH$). The reaction gives 6 mol of ethanol from 3 mol of ethyl acetate.

The ethanol producing step may be carried out, for example, at a temperature of 100 to 350° C. and a pressure of 0.1 to 20 MPa. In FIGS. 2 and 3, the esterification and hydrogenation are carried out in an apparatus. However, the invention is not limited to such case and the reactions may be carried out in different apparatuses continuously.

The reactions (Chemical Formulae 2 to 4) carried out in Step S1 to Step S3 are summarized to give the reaction shown in Chemical Formula (5), and 1 mol of hexose ($C_6H_{12}O_6$) can produce 3 mol of ethanol ($C_2H_5OH$). In this manner, the method for producing bioethanol of the embodiment is considered to be an ethanol producing process capable of using lignocellulose as a resource to a great extent.

$$C_6H_{12}O_6 + 6H_2 \rightarrow 3C_2H_5OH + 3H_2O \quad (5)$$

Furthermore, in the method for producing bioethanol of the embodiment, acetic acid can be produced from a substrate with high efficiency because the amount of cysteine added is reduced to suppress the growth of microorganisms during anaerobic acetic acid fermentation that uses the decomposition treatment solution of lignocellulose as a substrate and that uses *Clostridium thermoaceticum*. As a result, the yield of ethanol from lignocellulose can be also improved than in conventional methods.

EXAMPLES

Hereinafter, the advantages of the invention will be specifically described with reference to Examples and Comparative Examples of the invention.

Example 1

First, in Example 1, the acetic acid fermentation was performed with a varied amount of cysteine added to determine the ratio of a substrate used for the growth of microorganisms and the ratio of acetic acid produced. The fermentation was performed using *Clostridium thermoaceticum* as an anaerobic microorganism at a reaction temperature of 60° C. in a carbon dioxide atmosphere with stirring for 96 hours. The fermentation system included 5 ml of aqueous glucose solution (100 g/L) as a substrate, 5 ml of *Clostridium thermoaceticum* culture solution, 20 ml of buffer solution, and 20 ml of nutrient solution.

Table 2 shows the composition of the buffer solution used in Examples, Table 3 shows the composition of the nutrient solution, and Table 4 shows each amount of cysteine hydrochloride monohydrate in the fermentation system.

TABLE 2

| Component | Mixing amount |
|---|---|
| $KH_2PO_4$ | 0.94 g |
| $K_2HPO_4$ | 1.81 g |
| NaOH | 0.415 g |
| $NaHCO_3$ | 5 g |
| Distilled water | 400 ml |

TABLE 3

| Component | Mixing amount |
|---|---|
| Yeast extract | 5 g |
| $(NH_4)_2(SO_4)$ | 1 g |
| $MgSO_4·7H_2O$ | 0.25 g |
| $Fe(NH_4)_2(SO_4)_2·6H_2$ | 0.04 g |
| $NiCl_2·6H_2O$ | 0.00024 g |
| $ZnSO_4·7H_2O$ | 0.00029 g |
| $Na_2SeO_3$ | 0.000017 g |
| Resazurin | 0.001 g |
| Cysteine·HCl·$H_2O$ | 0~0.25 g |
| Distilled water | 400 ml |

TABLE 4

| | Cysteine concentration (g/L) |
|---|---|
| Comparative Example 1 | 0 |
| Example 1 | 0.05 |
| Example 2 | 0.10 |
| Comparative Example 2 | 0.15 |
| Comparative Example 3 | 0.20 |
| Comparative Example 4 | 0.25 |

Figure 4:
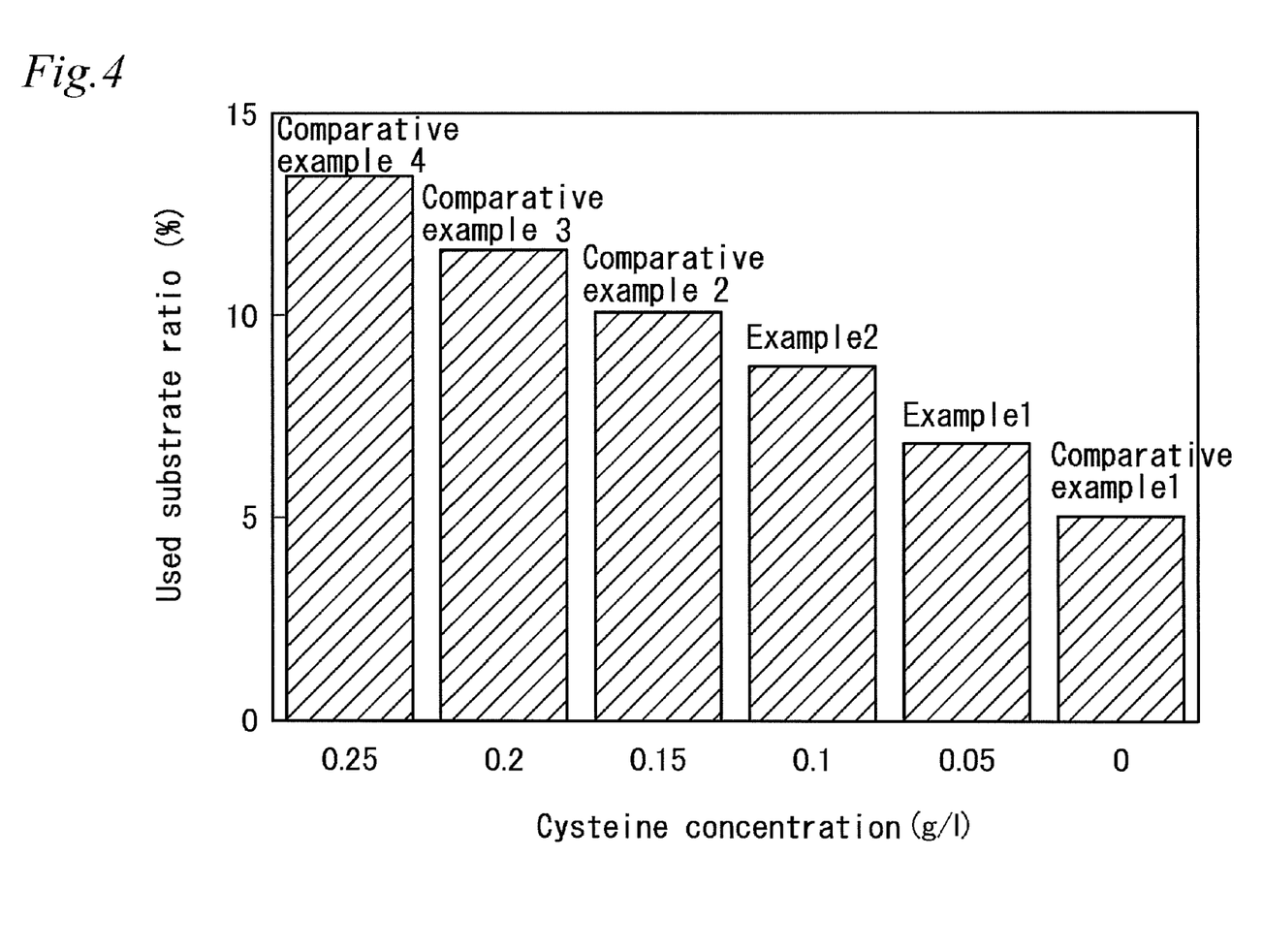
FIG. 4 is a graph showing the relationship between the amount of cysteine added and the ratio of the substrate used for the growth of microorganisms, where the cysteine concentration in the fermentation system is shown on the horizontal axis and the used substrate ratio is shown on the vertical axis.

FIG. 4 is a graph showing the relationship between the amount of cysteine added and the ratio of the substrate used for the growth of microorganisms, where the cysteine concentration in the fermentation system is shown on the horizontal axis and the used substrate ratio is shown on the vertical axis. The used substrate ratio shown in FIG. 4 is the ratio of the amount of the substrate used for the growth of microorganisms with respect to the amount of the substrate added, and can be determined by Equation (1).

Ratio of substrate used (%)={amount of substrate used for growth of microorganisms (g/L)/total amount of substrate (g/L)}×100     [Eq. 1]

Figure 5:
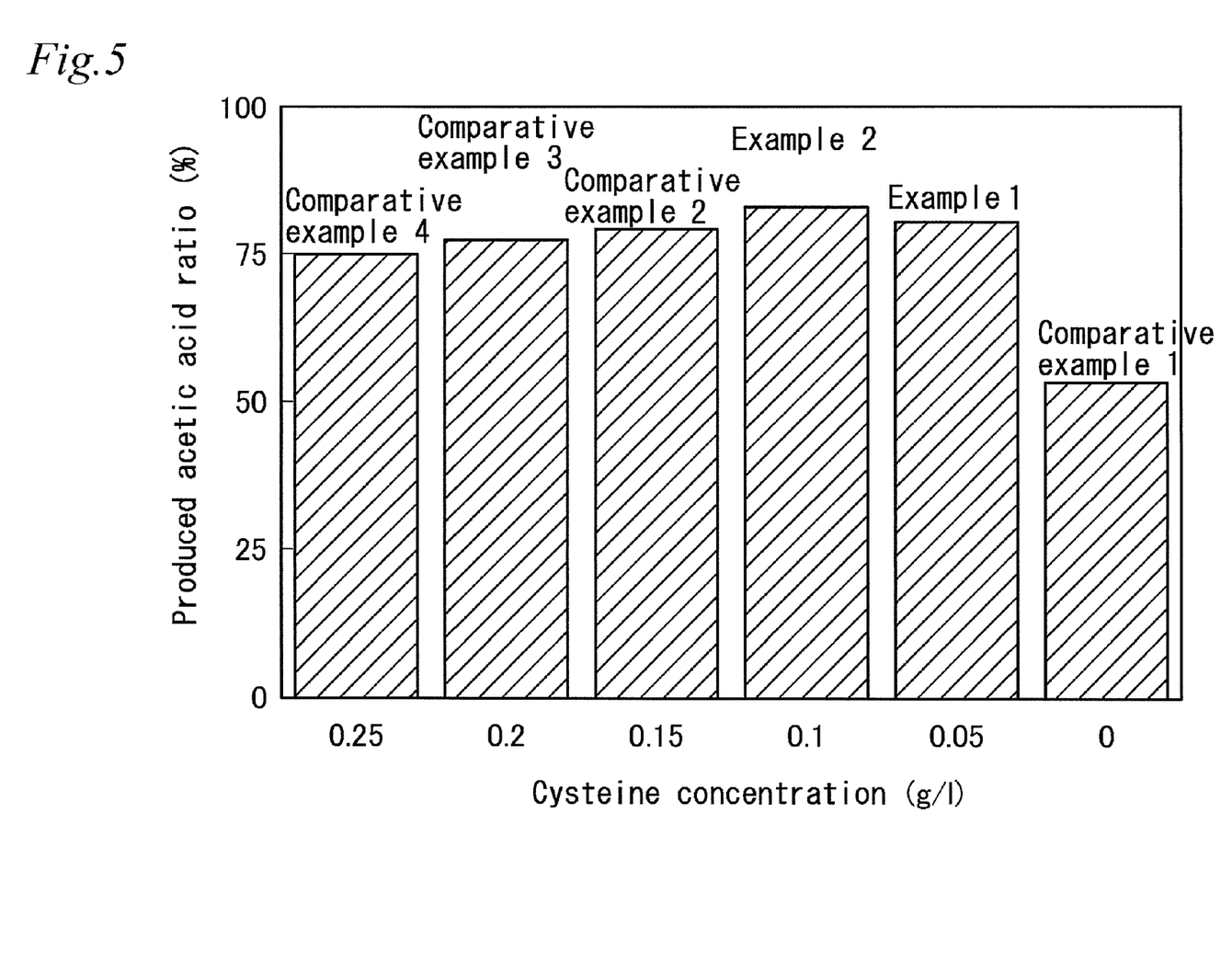
FIG. 5 is a graph showing the relationship between the amount of cysteine added and the ratio of acetic acid produced, where the cysteine concentration in the fermentation system is shown on the horizontal axis and the produced acetic acid ratio is shown on the vertical axis.

FIG. 5 is a graph showing the relationship between the amount of cysteine added and the ratio of acetic acid produced, where the cysteine concentration in the fermentation system is shown on the horizontal axis and the produced acetic acid ratio is shown on the vertical axis. The produced acetic acid ratio shown in FIG. 5 is the ratio of the amount of acetic acid produced with respect to the amount of the substrate added, and can be determined by Equation (2).

Ratio of acetic acid produced (%)={amount of acetic acid produced (g/L)/total amount of substrate (g/L)}×100     [Eq. 2]

As shown in FIGS. 4 and 5, Examples 1 and 2 where the amount of cysteine added was within the range according to the invention could reduce the amount of the substrate used for the growth of microorganisms and could increase the ratio of acetic acid produced. In contrast, in Comparative Examples 2 to 4 where a large amount of cysteine was added, the amount of the substrate used for the growth of microorganisms was high and the ratio of acetic acid produced was reduced. Meanwhile, in Comparative Example 1 without cysteine, the microorganism could not grow because of the lack of sulfur that is essential for growing the microorganism, and thus the amount of the substrate used for the growth of microorganisms was reduced to 5%, but the ratio of acetic acid produced was reduced to 54%, which is remarkably low as compared with other conditions.

From the results above, it was ascertained that the invention improved the conversion efficiency from a substrate into acetic acid.

Example 2

Figure 6:
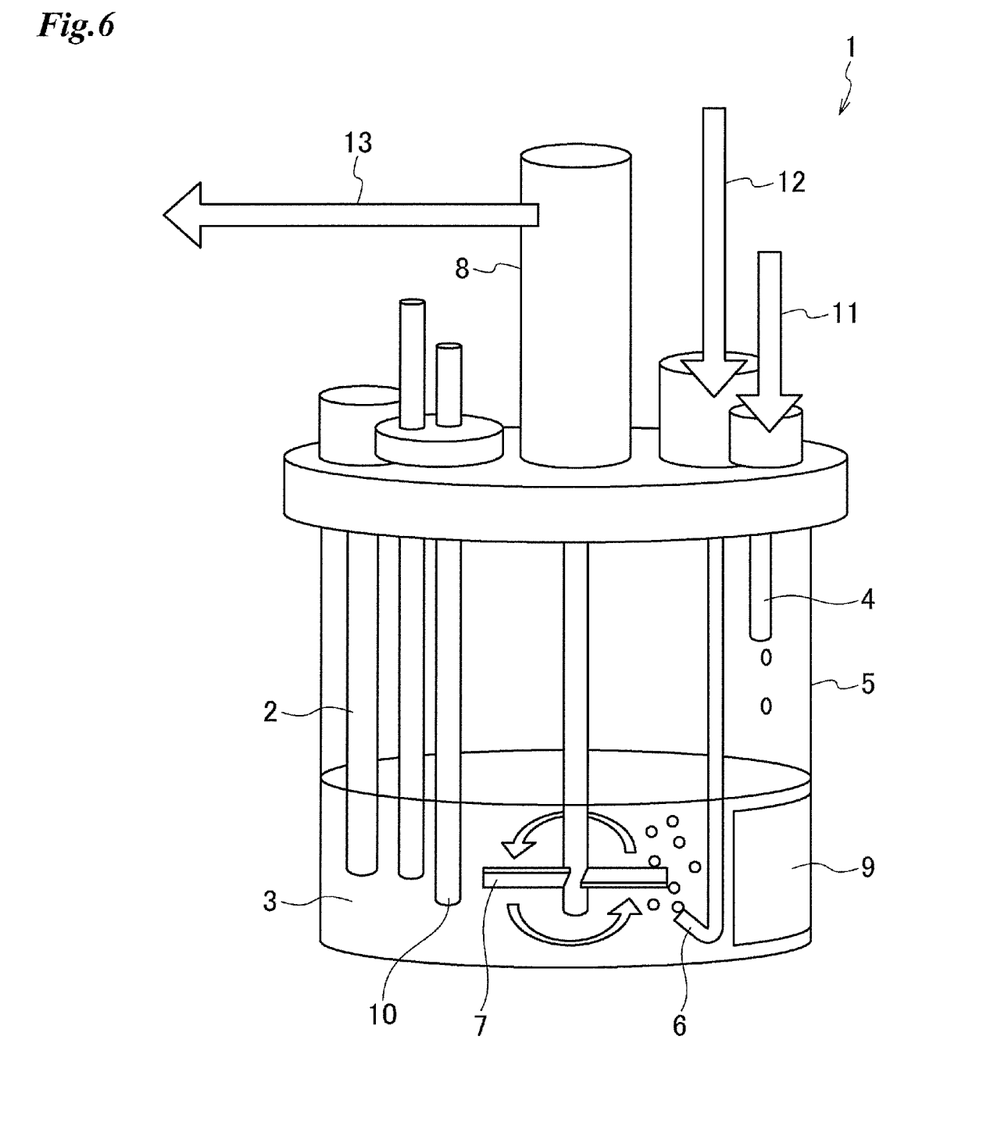
FIG. 6 is a schematic view showing the structure of a fermenter used in Example 2 of the invention.

Next, in Example 2 of the invention, acetic acid fermentation was performed using a fermenter. FIG. 6 is a schematic view showing the structure of a fermenter used in Example 2. As shown in FIG. 6, the fermenter 1 used in Example 2 could add an aqueous alkali solution 11 such as an aqueous sodium hydroxide solution through an aqueous alkali solution outlet 4, as needed, on the basis of pH of a fermentation medium 3 monitored with a pH meter 2.

Furthermore, a gas 12 could be directly fed from an external gas cylinder into a fermentation container 5. The fermentation container 5 had a gas outlet 6 at its lowest region and had blades 7 for stirring right above the gas outlet. Thus, in the fermenter 1, the gas 12 was fed through the gas outlet 6 and uniformly passed through the fermentation medium 3 by the rotating blades 7 for stirring for efficient bubbling.

Furthermore, in the fermenter 1, the gas 13 coming up to the liquid level was exhausted through a cooling tube 8 from the gas outlet to the outside, and consequently, the fermentation container 5 was constantly filled with the gas 12 alone from the gas cylinder to provide an absolute anaerobic condition. Moreover, a strip-shaped heater 9 was attached so as to cover the fermentation container 5, and consequently the temperature could be controlled as needed with a temperature sensor 10.

In Example 2, acetic acid fermentation of glucose (10 g/L) was firstly performed using the fermenter 1. The fermentation was performed using *Clostridium thermoaceticum* as an anaerobic microorganism at a reaction temperature of 60° C. in a carbon dioxide atmosphere with stirring. During the fermentation, a buffer solution was not used and 5 mol/L of aqueous sodium hydroxide solution was added as needed to maintain a solution pH at 7.0. The used nutrient solution had the same composition as in Table 3 except that the amount of cysteine hydrochloride monohydrate was 0.10 g.

Figure 7:
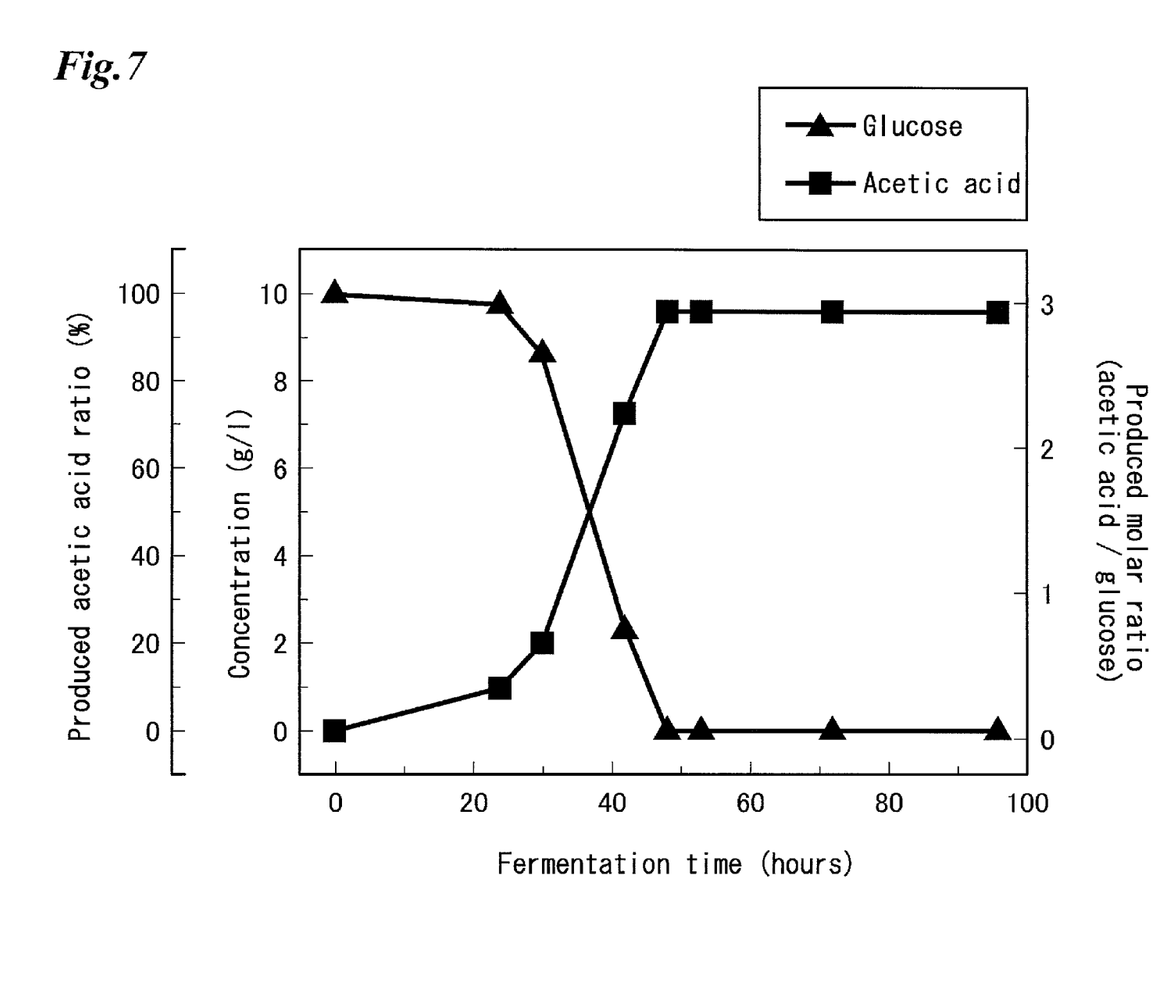
FIG. 7 is a graph showing the state of acetic acid fermentation, where the fermentation time is shown on the horizontal axis and the ratio of acetic acid produced and the molar ratio of acetic acid produced (acetic acid/glucose) are shown on the vertical axis.

FIG. 7 is a graph showing the state of acetic acid fermentation, where the fermentation time is shown on the horizontal axis and the ratio of acetic acid produced and the molar ratio of acetic acid produced (acetic acid/glucose) are shown on the vertical axis. As shown in FIG. 7, the acetic acid fermentation using the fermenter without a buffer solution produced 2.9 mol of acetic acid from 1 mol of glucose to achieve an produced acetic acid ratio of 96%.

Next, the amount of acetic acid produced was compared between a conventional fermentation method using a buffer solution and the fermentation method using the fermenter. For the comparison, *Clostridium thermoaceticum* and *Clostridium thermocellum* were used in combination as anaerobic microorganisms, a beechwood powder was treated at a constant pressure of 10 MPa and at 230° C. for 15 minutes and then at 270° C. for 15 minutes to prepare a pressurized hydrothermal treatment solution for the substrate.

Figure 8:
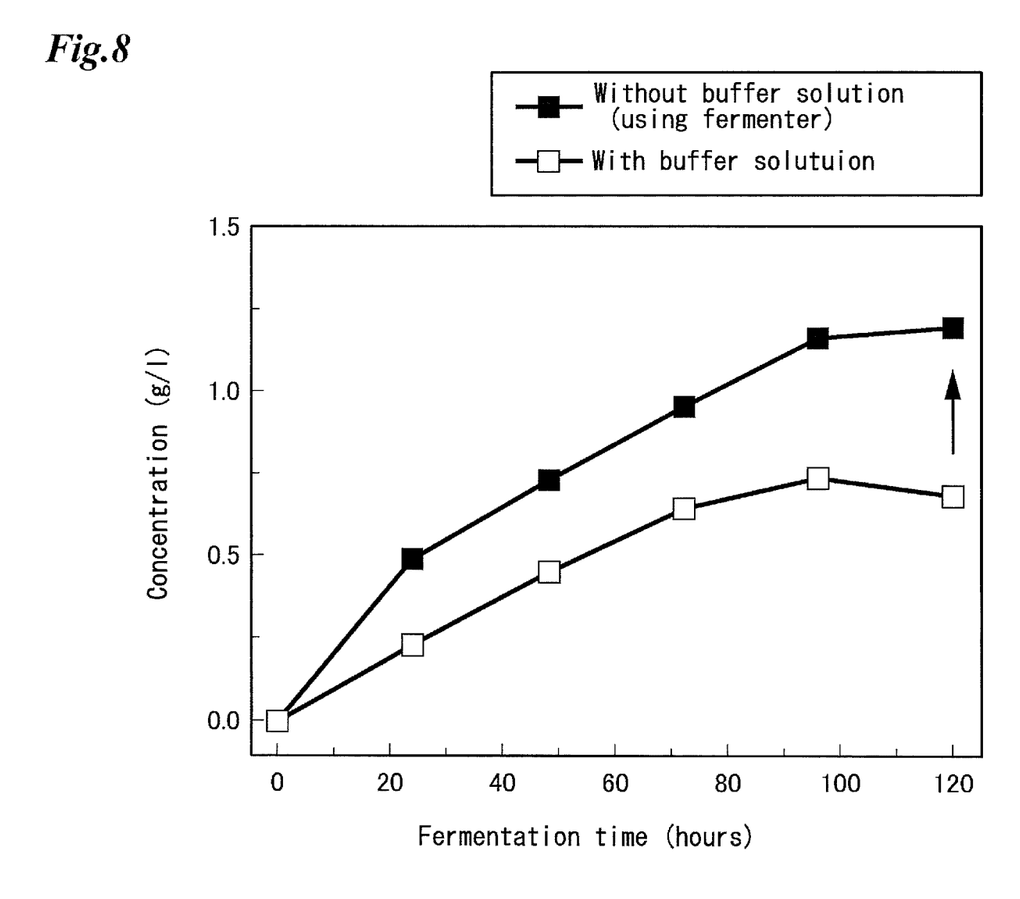
FIG. 8 is a graph showing the relationship between the presence of a buffer solution and the amount of acetic acid produced, where the fermentation time is shown on the horizontal axis and the concentration of acetic acid produced is shown on the vertical axis.

FIG. 8 is a graph showing the relationship between the presence of a buffer solution and the amount of acetic acid produced, where the fermentation time is shown on the horizontal axis and the concentration of acetic acid produced is shown on the vertical axis. As shown in FIG. 8, it was ascertained that the acetic acid fermentation using the fermenter without a buffer solution increased the amount of acetic acid produced as compared with the conventional acetic acid fermentation using a buffer solution.

The invention claimed is:

1. A method for producing acetic acid comprising a step of acetic acid-fermenting a substrate including a treatment solution obtained by decomposition treatment of lignocellulose using an anaerobic microorganism including *Clostridium thermoaceticum* in the presence of cysteine hydrochloride monohydrate at a concentration of 0.05 to 0.1 g/L.

2. The method for producing acetic acid according to claim 1, wherein an aqueous alkali solution is added on the basis of solution pH measured with a pH meter to maintain a solution pH within 6.5 to 7.5 during fermentation in the acetic acid fermentation step.

3. The method for producing acetic acid according to claim 1, wherein *Clostridium thermocellum* is used as the anaerobic microorganism in combination with *Clostridium thermoaceticum* in the acetic acid fermentation.

4. The method for producing acetic acid according to claim 1 further comprising a step of pressurized hydrothermal-treating lignocellulose to prepare a treatment solution, the treatment solution being used as the substrate in the acetic acid fermentation step.

5. The method for producing acetic acid according to claim 4, wherein the pressurized hydrothermal treatment is performed at a pressure of 0.11 to 50 MPa and a temperature of 130 to 400° C. for 0.1 second to 60 minutes.

6. The method for producing acetic acid according to claim 5, wherein the pressurized hydrothermal treatment includes a first treatment stage at a pressure of 0.11 to 50 MPa and a temperature of 130 to 270° C. for 1 to 60 minutes and a second treatment stage at a pressure of 0.11 to 50 MPa and a temperature of 230 to 400° C. and higher than the temperature in the first stage for 0.1 second to 60 minutes.

7. The method for producing acetic acid according to claim 1, wherein the substrate comprises at least a compound selected from the group consisting of hexoses, pentoses, glucuronic acid, organic acids, excessively decomposed saccharides and lignin-derived compounds.

8. The method for producing acetic acid according to claim 7, wherein the lignin-derived compounds comprises at least a compound selected from the group consisting of guaiacol, syringol, vanillin, syringaldehyde, coniferyl aldehyde, sinapyl aldehyde, coniferyl alcohol and sinapyl alcohol.

9. A method for producing acetic acid according to claim 1, further including producing bioethanol comprising a step of esterifying and hydrogenating the acetic acid.

* * * * *